United States Patent [19]

Schirmann et al.

[11] Patent Number: 5,990,364
[45] Date of Patent: *Nov. 23, 1999

[54] PURIFICATION OF PENTAFLUOROETHANE

[76] Inventors: Jean-Pierre Schirmann, 6 Rue de la Main d'Or, 75011 Paris; Serge Hub, 1 Rue Georges Courteline, 69100 Villeurbanne; Eric Lacroix, Le Bourg, 69480 Amberieux D'Azergues; Andre Lantz, Domaine de la Hetraie, 69390 Vernaison, all of France

[ * ] Notice: This patent issued on a continued prosecution application filed under 37 CFR 1.53(d), and is subject to the twenty year patent term provisions of 35 U.S.C. 154(a)(2).

[21] Appl. No.: 08/903,360

[22] Filed: Jul. 30, 1997

[30] Foreign Application Priority Data

Aug. 30, 1996 [FR] France ................................. 96 10633

[51] Int. Cl.⁶ .................................................. C07C 17/38
[52] U.S. Cl. ........................................... 570/177; 570/176
[58] Field of Search ...................... 570/176, 177

[56] References Cited

U.S. PATENT DOCUMENTS

| | | | |
|---|---|---|---|
| 4,873,381 | 10/1989 | Kellner et al. | 570/176 |
| 5,087,329 | 2/1992 | Felix . | |
| 5,346,595 | 9/1994 | Clemmer et al. . | |

FOREIGN PATENT DOCUMENTS

| | | |
|---|---|---|
| 612 709 | 2/1994 | European Pat. Off. . |
| 0626362 | 11/1994 | European Pat. Off. . |
| 0669302 | 8/1995 | European Pat. Off. . |
| WO 91/05752 | 5/1991 | WIPO . |
| WO 92/21147 | 11/1992 | WIPO . |
| WO 94/02439 | 2/1994 | WIPO . |
| WO 94/20441 | 9/1994 | WIPO . |

*Primary Examiner*—Alan Siegel

[57] ABSTRACT

In order to purify a crude pentafluoroethane (F125) containing chloropentafluoroethane (F115), it is subjected to a heat treatment in the presence of hydrogen, the treatment being carried out at a temperature at least equal to 550° C. and with an $H_2$/F115 molar ratio of at least 10.

21 Claims, No Drawings

PURIFICATION OF PENTAFLUOROETHANE

FIELD OF THE INVENTION

The present invention relates to the field of fluorinated hydrocarbons and has more particularly as subject the purification of pentafluoroethane (hereinafter F125) containing chloropentafluoroethane (F115).

BACKGROUND OF THE INVENTION

F125 is one of the hydrofluorocarbons (HFCs) used in the context of the substitution of chlorofluorocarbons (CFCs) and of hydrochlorofluorocarbons (HCFCs) which are already banned or in the course of being banned because of their harmful effect on the atmospheric ozone layer.

A number of access routes to F125 are known. The oldest consists in reacting tetrafluoroethylene with hydrofluoric acid in the presence of a catalyst. A particularly pure F125 is obtained in this way but with a cost which rules out any large-scale application in the field of commercial refrigeration or domestic air conditioning.

Recently proposed industrial processes all start with a starting material available in very large amounts at a very low price, perchloroethylene $CCl_2=CCl_2$. A known industrial process consists in fluorinating perchloroethylene to F115 and in then hydrogenolysing the latter in the presence of a catalyst, in particular of a palladium catalyst. However, such a process is unsatisfactory because the conversion of the F115 is incomplete. The boiling points of F125 and of F115 are very similar and a simple distillation does not make it possible to separate the two components and thus to obtain pure F125.

The catalytic fluorination of perchloroethylene, in one or a number of stages, also produces not insignificant amounts (several thousands of ppm) of F115 in the crude F125 obtained.

Thus, whatever the process for the synthesis of F125 from perchloroethylene, the same problem is posed of the purification of the F125 in order to remove the F115 therefrom. This purification has thus formed the subject of much research and some solutions have already been disclosed.

U.S. Pat. No. 5,087,329 and Patent Applications EP 0,626,362, WO 92/21147 and EP 0,669,302 have provided the extractive distillation of the crude F125 using a solvent, such as, for example, an optionally halogenated hydrocarbon. However, this technique requires significant investments. It is likewise the case with the technique described in U.S. Pat. No. 5,346,595, which consists in subjecting the crude F125 to two successive distillations, one under superatmospheric pressure and the other under reduced pressure. It is not economically possible with these techniques to achieve very low F115 contents (less than 100 ppm).

Provision has also been made, in Patent EP 0,612,709, for the treatment of F125+F115 mixtures with hydrofluoric acid in the vapour phase over a catalyst, in order to convert the F115 to hexafluoroethane (F116). However, this process results in a pointless consumption of hydrofluoric acid and in the formation of a by-product with an economic value which is difficult to recover.

Application WO 94/02439 describes a process for the hydrogenolysis of the F125+F115 mixture over a hydrogenation catalyst at a temperature of between 300 and 600° C. This technique is particularly effective but results in the production, as by-products, of 1,1,1,2-tetrafluoroethane (F134a) and especially of 1,1,1-trifluoroethane (F143a) which are difficult to separate by distillation.

The reactivity of CFCs with respect to hydrogen is known and Patent Application WO 91/05752 shows that it is possible to synthesize HFCs from CFCs and hydrogen in an empty reactor. However, this publication does not mention the purification of the HFCs and the operating conditions recommended for the synthesis do not result in an effective purification.

DESCRIPTION OF THE INVENTION

It has now been found, and it is this which forms the subject of the present invention, that an F125 containing a few thousand ppm of F115 can be purified by subjecting the crude impure F125 to a heat treatment in the presence of hydrogen at a temperature of at least 550° C. and with an $H_2$/F115 molar ratio at least equal to 10. It is thus possible to obtain a particularly pure commercial F125 containing less than 100 ppm of F115.

This particularly simple and effective heat treatment does not cause the production, as a by-product, of F143a, which is difficult to separate from F125.

The process according to the invention is implemented at a temperature of at least 550° C., generally of between 550 and 1000° C., preferably between 600 and 700° C. The operating pressure can be between 0.1 and 100 bar absolute but it is preferable to operate at atmospheric pressure or at a pressure which can range up to 20 bar.

The $H_2$/F115 molar ratio is at least equal to 10 and can range up to 1500 but it is generally preferable to operate at a molar ratio of between 50 and 1200 and more particularly between 80 and 1000. Given the absence of catalyst in the reactor, the purity of the hydrogen used does not have to be as high as that commonly required to maintain the activity of a catalyst based on a precious metal. This constitutes another advantage of the process according to the invention.

The treatment according to the invention is advantageously carried out in a reactor made of molybdenum, titanium, nickel, iron, cobalt and their alloys which can also contain chromium and/or tungsten. Inconel 600 or Hastelloy is preferably used industrially. The reactor can be empty or, to facilitate contact of the reactants, filled with a packing composed of particles or of fashioned shapes made of molybdenum, titanium, nickel, iron or cobalt or made of an inert material, such as silicon carbide or carbon with a low specific surface.

The flow of the reactants (crude F125 and $H_2$) entering into the reactor can be diluted with an inert gas, such as helium or nitrogen. The residence time of the reaction mixture can vary within wide limits, depending on the F115 content of the crude F125 to be purified and on the chosen operating conditions (temperature, pressure, $H_2$/F115 molar ratio). It is generally between 0.1 and 200 seconds, preferably between 1 and 100 seconds.

EXAMPLES

The following examples illustrate the invention without limiting it. The concentrations are expressed as volume per million (vpm).

Examples 1 to 5

The operation was carried out at atmospheric pressure in a tubular reactor made of Inconel 600, with a length of 47 cm and with an internal diameter of 2.1 cm, placed in an electric furnace with a power of 1.5 kW; the temperature of the furnace was measured using a thermocouple.

The reactants (crude F125 and $H_2$) were introduced simultaneously and continuously via mass flowmeters which enable the flowrates and thus the molar ratios to be controlled.

The gaseous products were analysed by in-line chromatography (VPC) at the outlet of the reactor.

The operating conditions and the results obtained by using a crude F125 containing 750 vpm of F115 and 45 vpm of F143a are summarized in the following table. As the analytical errors for these compounds are estimated at plus or minus 5% for F115 and at plus or minus 10% for F143a, F115 contents of between 710 and 790 vpm and F143 a contents of between 40 and 50 vpm are not significantly different from the starting concentrations.

| | EXAMPLE | | | | |
|---|---|---|---|---|---|
| | 1, Comparative | 2 | 3 | 4 | 5 |
| Operating conditions: | | | | | |
| Temperature (° C.) | 500 | 550 | 580 | 600 | 600 |
| H₂ Flowrate (1/h) | 0.5 | 0.5 | 0.5 | 0.8 | 1.1 |
| F125 Flowrate (1/h) | 6.5 | 6.5 | 6.5 | 7.2 | 7.2 |
| H₂/F115 Molar ratio | 103 | 103 | 103 | 148 | 204 |
| Results: | | | | | |
| Content (vpm) of the F12S in: | | | | | |
| F115 | 620 | 480 | 250 | 150 | 70 |
| F143a | 45 | 50 | 45 | 40 | 30 |

Examples 6 to 9

The tests were carried out at atmospheric pressure in a tubular reactor identical to the above by using a crude F125 containing 710 vpm±5% of F115 and 60 vpm±10% of F143a.

The operating conditions and the results obtained are summarized in the following table:

| | EXAMPLE | | | |
|---|---|---|---|---|
| | 6 | 7, Comparative | 8, Comparative | 9, Comparative |
| Operating conditions: | | | | |
| Temperature (° C.) | 700 | 400 | 450 | 600 |
| H₂ Flowrate (1/h) | 4.8 | 1.1 | 1.1 | 0.05 |
| F125 Flowrate (1/h) | 31 | 7.2 | 7.2 | 14.9 |
| H₂/F115 Molar ratio | 215 | 212 | 212 | 5 |
| Results: | | | | |
| Content (vpm) of the F125 in: | | | | |
| F115 | 140 | 710 | 710 | 680 |
| F143a | 70 | 55 | 55 | 60 |

Example 10

A stream of 8.4 l/h of hydrogen and of 31 l/h of a crude F125 containing 8000 vpm of F115 and 60 vpm of F143a was passed, at atmospheric pressure and at 700° C., into a tubular reactor identical to the above.

At the outlet of the reactor, the F115 content had fallen to 3600 vpm and the F143 a content was 70 vpm.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the purification of a crude pentafluoroethane containing chloropentafluoroethane (F115), comprising:
subjecting the crude pentafluoroethane to a heat treatment in a reactor without an added catalyst, in the presence of hydrogen at a temperature of at least about 700° C. and with an $H_2/F115$ molar ratio at least equal to 10; and
recovering purified pentafluoroethane with less than 100 ppm of F115.

2. Process according to claim 1, wherein the treatment is carried out at a temperature up to 1000° C.

3. Process according to claim 1, wherein the treatment is carried out at a pressure of between 0.1 and 100 bar absolute.

4. Process according to claim 1, wherein the $H_2/F115$ molar ratio is between 10 and 1500.

5. Process according to claim 1, wherein the treatment is carried out in a reactor made of molybdenum, titanium, nickel, iron, cobalt and their alloys optionally containing chromium and/or tungsten.

6. Process according to claim 1, wherein the residence time is between 0.1 and 200 seconds.

7. Process according to claim 3, wherein the pressure is atmospheric pressure.

8. Process according to claim 3, wherein the pressure ranges up to 20 bar.

9. Process according to claim 4, wherein the molar ratio is between 50 and 1200.

10. Process according to claim 4, wherein the molar ratio is between 80 and 1000.

11. Process according to claim 5, wherein the reactor is made of Inconel 600 or Hastelloy.

12. Process according to claim 6, wherein the residence time is between 1 and 100 seconds.

13. Process according to claim 1 wherein F143a is not produced as a byproduct.

14. Process for the purification of a crude pentafluoroethane containing chloropentafluoroethane (F115), comprising:
subjecting the crude pentafluoroethane to a heat treatment in a reactor without an added catalyst, in the presence of hydrogen, at a temperature of at least about 700° C., at a pressure of from 0.1 bar to 100 bar and with an $H_2/F115$ molar ratio of from 10 to 1500;
said reactor being made of material selected from the group consisting of molybdenum, titanium, nickel, iron, cobalt and alloys thereof; and
recovering purified pentafluoroethane without producing F143 a as a byproduct.

15. Process according to claim 14 wherein the alloys contain chromium and/or tungsten.

16. Process according to claim 14 wherein the reactor is made of Inconel 600 or of Hastelloy.

17. Process according to claim 14 wherein the purified pentafluoroethane is recovered with less than 100 ppm of F115.

18. Process according to claim 14 wherein the heat treatment is carried out with an $H_2/F115$ molar ratio of from 80 to 1000.

19. Process according to claim 14 wherein residence time is between 0.1 and 200 seconds.

20. Process according to claim 14 wherein residence time is between 1 and 100 seconds.

21. Process for the purification of a crude pentafluoroethane containing chloropentafluoroethane (F115), consisting essentially of:
subjecting the crude pentafluoroethane to a heat treatment in a reactor without an added catalyst, in the presence of hydrogen, at a temperature of at least about 700° C. at a pressure of from 0.1 bar to 100 bar and with an $H_2/F115$ molar ratio of from 10 to 1500;
said reactor being made of material selected from the group consisting of molybdenum, titanium, nickel, iron, cobalt and alloys thereof; and
recovering purified pentafluoroethane.

* * * * *